(12) United States Patent
Nezafat et al.

(10) Patent No.: US 7,787,930 B2
(45) Date of Patent: Aug. 31, 2010

(54) ADIABATIC $T_2$ PREPARATION SEQUENCE FOR MAGNETIC RESONANCE IMAGING WITH REDUCED $B_1$ SENSITIVITY

(75) Inventors: Reza Nezafat, Bethesda, MD (US); Ronald Ouwerkerk, Baltimore, MD (US); Matthias Stuber, Ellicott City, MD (US)

(73) Assignees: The United States of America as represented by the Department of Health and Human Services, Washington, DC (US); The Johns Hopkins University, Baltimore, MD (US)

( * ) Notice: Subject to any disclaimer, the term of this patent is extended or adjusted under 35 U.S.C. 154(b) by 371 days.

(21) Appl. No.: 11/147,151

(22) Filed: Jun. 6, 2005

(65) Prior Publication Data
US 2006/0253015 A1 Nov. 9, 2006

Related U.S. Application Data

(60) Provisional application No. 60/674,949, filed on Apr. 25, 2005.

(51) Int. Cl.
*A61B 5/00* (2006.01)
(52) U.S. Cl. ............... 600/410; 324/307; 324/309; 600/413
(58) Field of Classification Search ........... 600/410, 600/411, 413; 324/307, 312, 306, 309
See application file for complete search history.

(56) References Cited

U.S. PATENT DOCUMENTS

| | | | | |
|---|---|---|---|---|
| 4,695,799 A | * | 9/1987 | Hardy et al. | ............... 324/307 |
| 4,914,392 A | * | 4/1990 | Ugurbil et al. | ............... 324/309 |
| 4,988,947 A | * | 1/1991 | Ugurbil et al. | ............... 324/307 |
| 5,019,784 A | | 5/1991 | Garwood et al. | |
| 5,320,099 A | * | 6/1994 | Roberts et al. | ............... 600/413 |
| 5,588,431 A | * | 12/1996 | Mani et al. | ............... 600/410 |
| 5,655,531 A | | 8/1997 | Nishimura et al. | |
| 6,492,809 B1 | * | 12/2002 | Speier et al. | ............... 324/303 |
| 6,518,757 B1 | * | 2/2003 | Speier | ............... 324/303 |
| 6,674,282 B2 | * | 1/2004 | Pines et al. | ............... 324/307 |
| 6,750,649 B1 | * | 6/2004 | Rosenfeld | ............... 324/307 |
| 6,809,518 B2 | * | 10/2004 | Beaudoin et al. | ............... 324/314 |
| 6,844,728 B2 | * | 1/2005 | Speier et al. | ............... 324/303 |

(Continued)

OTHER PUBLICATIONS

R Nezafat, M Stuber, R Ouwerkerk, AM Gharib, MY Desai, RI Pettigrew. B1-Insensitive T2 Preparation for Improved Coronary Magnetic Resonance Angiography at 3 T. Magnetic Resonance in Medicine 55: 858-864 (2006).*

Barker et al., "Broadband Proton Decoupling for In Vivo Brain Spectroscopy in Humans," Magn. Reson. In Medicine 45:226-232 (2001).

(Continued)

*Primary Examiner*—Brian Casler
*Assistant Examiner*—Amanda Lauritzen
(74) *Attorney, Agent, or Firm*—Klarquist Sparkman, LLP

(57) ABSTRACT

Adiabatic pulses that define an amplitude modulation and a frequency modulation are applied in a sequence of pulses to obtain a $T_2$ weighted magnetic resonance image. Such an adiabatic $T_2$ prep sequence typically includes a first 90° pulse, an even number of adiabatic pulses, and a second 90° pulse. Adiabatic pulses can be selected based on function pairs, or can be defined numerically. A magnetic resonance imaging (MRI) system includes a library of adiabatic pulse waveforms, and is configured to select a waveform and apply an RF magnetic field based on the selected pulse waveform.

30 Claims, 6 Drawing Sheets

U.S. PATENT DOCUMENTS

| | | | | |
|---|---|---|---|---|
| 7,064,545 | B2* | 6/2006 | Zaharchuk et al. | 324/307 |
| 7,315,756 | B2* | 1/2008 | Yarnykh et al. | 600/411 |
| 2003/0020473 | A1* | 1/2003 | Speier et al. | 324/303 |
| 2005/0024052 | A1 | 2/2005 | Bendall et al. | |
| 2005/0030026 | A1* | 2/2005 | Pines et al. | 324/309 |
| 2007/0255129 | A1* | 11/2007 | Du et al. | 600/410 |

OTHER PUBLICATIONS

Beaudoin et al., "The pseudo-adiabatic RF pulse: a fast adiabatic quality RF pulse with low SAR," Proc. Intl. Soc. Magn. Reson. 10 (2002).

Botnar et al., "Improved Coronary Artery Definition With T2-Weighted, Free-Breathing, Three-Dimensional Coronary MRA," Circulation 99:3139-3148 (1999).

Brittain et al., "Coronary Angiography with Magnetization-Prepared $T_2$ Contrast," MRM 33:689-696 (1996).

Nezafat et al., "$B_1$-Insensitive $T_2$ Preparation for Improved Coronary Magnetic Resonance Angiography at 3 T," Mag. Reson. in Medicine 55:858-864 (2006).

Norris, David G., "Adiabatic Radiofrequency Pulse Forms in Biomedical Nuclear Magnetic Resonance," Concepts in Magnetic Resonance 14:89-101 (2002).

Rosenfeld et al., "Is the sech/tanh Adiabatic Pulse Really Adiabatic?" J. Magn. Reson. 132:102-108 (1998).

Tannus et al., "Adiabatic Pulses," NMR in Biomedicine 10:423-434 (1997).

Tesiram et al., "Universal Equations for Linear Adiabatic Pulses and Characterization of Partial Adiabaticity," J. Magn. Reson. 156:26-40 (2002).

* cited by examiner

FIG. 3
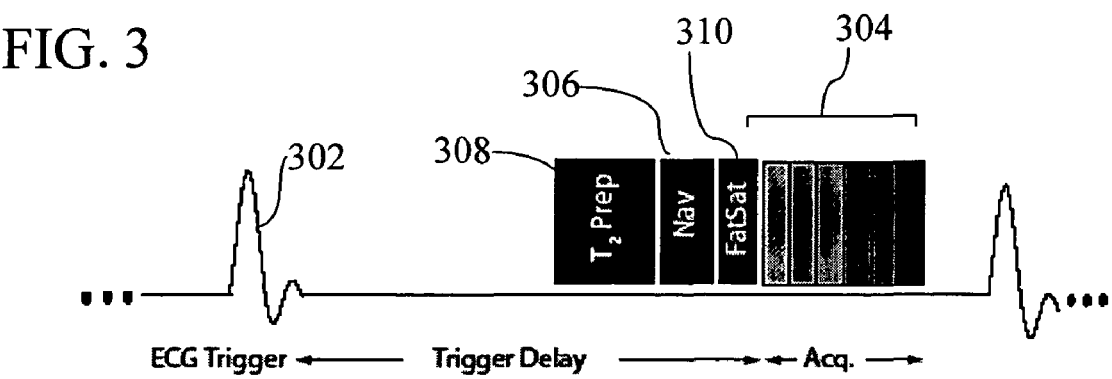
FIG. 4B
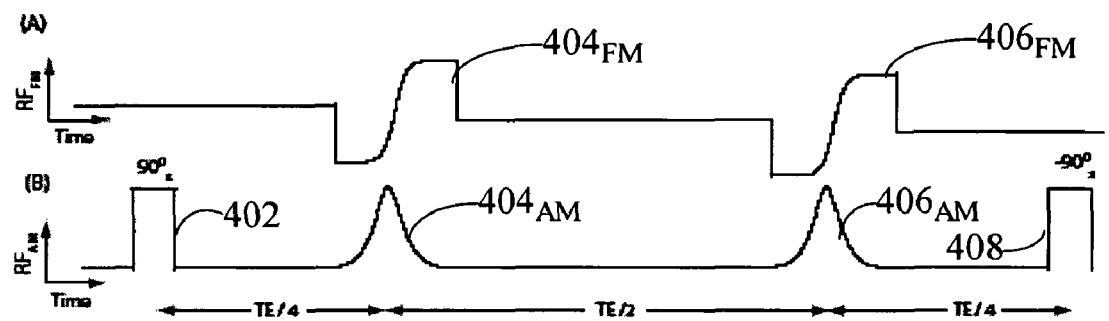
FIG. 4A

ADIABATIC $T_2$ PREPARATION SEQUENCE FOR MAGNETIC RESONANCE IMAGING WITH REDUCED $B_1$ SENSITIVITY

CROSS REFERENCE TO RELATED APPLICATIONS

This application claims the benefit of U.S. Provisional Patent Application No. 60/674,949, filed Apr. 25, 2005, which is hereby incorporated herein by reference.

STATEMENT CONCERNING GOVERNMENT SUPPORT

This invention was made by an agency of the United States Government, and the United States Government has certain rights in this invention.

TECHNICAL FIELD

The disclosure pertains to apparatus for magnetic resonance imaging.

BACKGROUND

Modern medical imaging methods permit physicians to more accurately diagnose and treat a wide variety of disorders. Such imaging methods are based on various technologies including acoustic waves (ultrasound), radioactive decay (positron emission tomography), and nuclear magnetic resonance (magnetic resonance imaging). Each of these imaging techniques has its own characteristic advantages and disadvantages, but medical researchers, physicians and other practitioners continue to seek higher resolution, more reliable, less invasive, and more easily interpretable imaging systems and methods in many applications. For example, coronary magnetic resonance angiography (MRA) has been used in the assessment of coronary disease. Unfortunately, the low signal-to-noise ratio (SNR) obtained at applied fields of about 1.5 T can limit the application of this technique for distal and branching vessels. Application of higher magnetic fields can improve SNR but higher magnetic fields are associated with undesirable changes in off-resonance susceptibilities, magnetic field inhomogeneities, and increased specific absorption rate (SAR).

Magnetic resonance (MR) imaging systems generally use a static magnetic field ($B_0$) and a radio frequency magnetic field ($B_1$) to produce images. Unfortunately, these magnetic fields cannot be controlled with arbitrary precision, and MR signals and images can be degraded by imperfections such as non-uniformities in these magnetic fields. All $T_2$ prep sequences consist of an initial 90° pulse to convert a substantial part of the longitudinal magnetization in the image field of view to transverse magnetization, a combination of delays and RF pulses designed to refocus this transverse magnetization after some signal decrease through $T_2$ relaxation during these pulses and delays, followed by a final 90° pulse to return a substantial part of the refocused magnetization to longitudinal magnetization. The $T_2$ relaxation between the two 90° pulses provides the desired alteration of contrast between components of the sample with different $T_2$ relaxation rates. Conventional $T_2$ preparation ($T_2$ prep) sequences have been designed to be robust to flow as well as to inhomogeneites in both $B_0$ and $B_1$. Such sequences use opposing pairs of so-called Malcom-Levitt (MLEV) pulses that can compensate pulse shape imperfections in the RF magnetic field $B_1$. Two representative sequences of such MLEV weighted composite $T_2$ prep sequences are shown in FIGS. 1A-1B. Pulses indicated as $180_x°$ are composite pulses, each consisting of a $90°_x$ $180°_y$ $90°_x$ pulse sequence. Such MLEV weighted composite pulses can compensate some imperfections in $B_1$, with larger numbers of such pulses providing increased compensation. However, increasing the number of MLEV pulses results in an increase in specific absorption rate (SAR), thus limiting the use of large numbers of MLEV pulses, especially at high $B_0$. Thus, MLEV pulse based $T_2$ prep is unsatisfactory in many applications.

Three dimensional (3D) MRA can be used to image the tortuous path of the coronary artery tree with improved SNR relative to two dimensional MRCA. Unfortunately, 3D coronary MRA images have a low contrast between coronary blood and myocardium. Image contrast can be enhanced with contrast agents or non-endogenous magnetization sequences. $T_2$ prep contrast enhancement can be used to increase contrast between blood in coronary arteries and surrounding tissues based on an applied $T_2$ weighting. However, $T_2$ prep is associated with imaging artifacts that limit clinical utility, and can be associated with unacceptable SAR. Accordingly, improved methods and apparatus are needed, particularly for $T_2$-weighted imaging.

SUMMARY

Methods and apparatus are described that provide $T_2$-weighted magnetic resonance images and magnetic resonance signals based on application of pulse sequences that include one or more adiabatic pulses. Such sequences can be referred to as adiabatic $T_2$ preparation sequences (adiabatic $T_2$ prep). Adiabatic pulses combine amplitude and frequency modulation of the RF designed to create a rotation of the magnetization in a way that is independent of the RF field strength over a substantial range of RF field strength variations. Typically, adiabatic pulses are provided as substitutes for 180° pulses, and generally provide images that are superior to those obtained with only amplitude modulation 180° pulses, or other so-called "hard" radio-frequency (RF) pulses that have a time invariant amplitude over their duration.

Magnetic resonance systems comprise a system controller configured to define an adiabatic pulse and a radiofrequency (RF) coil configured to produce an RF magnetic field based on the adiabatic pulse defined by the system controller. A receiver coil is configured to produce a detected signal based on a specimen magnetization processed by the excitation pulse and subsequent imaging sequence of gradient and or RF waveforms, and an image processor is configured to produce a specimen image based on the detected signal.

According to representative examples, magnetic resonance imaging methods comprise applying pulse sequences that include rotating at least a portion of a longitudinal magnetization of a specimen into a transverse plane to establish a transverse magnetization, a process that can be referred to as excitation. Excitation can be produced with, a selective pulse in combination with a magnetic field gradient to select a slice of a thickness determined by the pulse excitation bandwidth and the gradient strength and orientation. In other examples a part of the longitudinal magnetization determined by the pulse parameters and the RF coil characteristics can be rotated into the transverse plane by a non-selective pulse for example, with a hard 90° pulse or an adiabatic half passage pulse. The magnetization is collected during an acquisition period with an RF coil that can be either the same coil used for the excitation or a dedicated receiver coil. The voltage of the receiver coil during the acquisition period is amplified and digitized in a manner to preserve the phase of the received RF signal relative to the phase of the excitation RF. This process can be referred to as an excitation cycle and may be repeated after a repetition delay order to either increase the signal to noise ratio by signal averaging, or to further encode the signal for spatial position of the spins, or both. In representative examples the specimen includes a heart or a portion of a heart, and image acquisition is triggered based on cardiac activity. In other examples the repetition delay is selected to let the longitudinal magnetization fully or partially recover. The transverse magnetization is coded before and during the data acquisition interval for spatial position by applying a combination of magnetic field gradients, modulated as a function of time, and in some examples additional RF pulses are applied, the phase and or amplitude of which are modulated within one excitation cycle or varied between excitation cycle to encode spatial position of the spins into the amplitude and phase of the received signal. In representative examples, a computer readable medium such as RAM, DRAM, flash memory, a CDROM, a floppy disk, or a hard disk contains computer executable instructions for such imaging methods.

Imaging cycles of such imaging methods can be preceded by a $T_2$-prep sequence to alter the image contrast. In a $T_2$-prep sequence the longitudinal magnetization is converted to transverse magnetization and is then refocused by one or more inversion pulses, such that the transverse magnetization is refocused at the end of the sequence. The resulting refocused component of the transverse magnetization is then converted back to longitudinal magnetization as a starting point for an imaging sequence. In representative examples of the $T_2$-prep sequence, the excitation pulse consists of a block pulse or an adiabatic half passage pulse that is followed after a delay $d_1$ by an adiabatic radio-frequency (RF) inversion pulse having an amplitude modulation and a frequency modulation, and configured to invert a substantial component of the transverse magnetization. After a second delay $d_2$, a second adiabatic radio-frequency (RF) inversion pulse having an amplitude modulation, phase modulation and configuration substantially the same as the first adiabatic inversion pulse is applied, such that a substantial component of the transverse magnetization is inverted again. After this second adiabatic inversion pulse and a third delay $d_3$, typically equal to $d_1$, a 90° pulse is applied to rotate the refocused transverse magnetization back to a longitudinal magnetization to produce a $T_2$ weighted longitudinal magnetization. The excitation pulse of the subsequent imaging sequence will therefore result in $T_2$ weighted transverse magnetization.

In representative examples, the first and second adiabatic RF inversion pulses have a common waveform, and the first and second RF magnetic fields are along a common axis. In other representative examples the adiabatic RF inversion pulses have waveforms based on mathematical functions such that the amplitude modulation is based on a hyperbolic secant function, and the frequency modulation is based on a hyperbolic tangent function. In other examples, the amplitude and frequency modulation waveforms are described by different functions or are numerically calculated to obtain the desired inversion over a given bandwidth or range of $B_1$ field variations.

In additional examples, the frequency modulation waveform is encoded as an RF phase modulation waveform that is proportional to the time derivative of the frequency yielding a response comparable to that of a frequency modulated pulse. This phase modulation may be modified by an optional phase ramp to change the effective center frequency of the pulse response function. In other examples the adiabatic inversion pulses derive the desired frequency sweep from a combination of a frequency modulation of the RF field and a time varying magnetic field gradient, selected so that the adiabatic inversion required for the adiabatic $T_2$-prep sequence is achieved in a specific part of the sample, while suppressing signals elsewhere. In other examples the adiabatic inversion pulses are not truly adiabatic, but have a combination of frequency or phase modulation and amplitude modulations, akin to those of truly adiabatic pulses, that provides an inversion that is substantially independent of $B_1$ field variations over a selected range.

In additional representative examples of the adiabatic $T_2$-prep sequence, the MR system controller is configured to define a pulse sequence that includes a first 90° pulse, a first instance of the adiabatic pulse, a second instance of the adiabatic pulse, and a second 90° pulse, and the receiver coil is configured to produce the detected signal based on the specimen magnetization produced with the pulse sequence. In further examples of the adiabatic $T_2$-prep sequence, the system controller is configured to define at least one of the first 90° pulse or the second 90° pulse as a composite pulse. In still other examples of the adiabatic $T_2$-prep sequence, the system controller includes a user interface configured to receive a user input associated with selection of the adiabatic pulse. In further examples, the system controller includes a computer readable medium having stored thereon a plurality of adiabatic pulse definitions, and the system controller is configured to define the adiabatic pulse by selecting from among the plurality of adiabatic pulse definitions. In other examples, the system controller is configured to select an echo time to alter the contrast between components of the sample with differing $T_2$ relaxation rates. In further illustrative examples, the adiabatic pulse is defined based on a first function and a second function that define an amplitude modulation portion and a frequency modulation portion, respectively. In further examples, a trigger input is configured to receive a trigger signal associated with an electrocardiogram.

Methods of reducing magnetic resonance image sensitivity to variations in a main magnetic field inhomogeneities and RF penetration in $T_2$-weighted images comprise applying a first 90° pulse, a first adiabatic pulse after an interval $d_1$ of about TE/4, wherein TE is an echo time, a second adiabatic pulse after an interval $d_2$ of about TE/2, and a second 90° pulse after an interval $d_3$ of about TE/4. In some examples, adiabatic, pseudo-adiabatic, or quasi-adiabatic half passage pulses are used instead of hard 90° pulses. An image signal is obtained based on a magnetization produced by applying the series of pulses. In some examples, the first and second 90° pulses are composite pulses. In other examples, the first adiabatic pulse and the second adiabatic pulse have a common waveform. In further examples, the common waveform is defined by a pair of functions that define an amplitude portion and a frequency portion. In additional examples, the common waveform is defined by a numerically defined amplitude modulation and a numerically defined frequency modulation. In other examples, the image signal is processed to form a coronary magnetic resonance angiogram.

These and other features and advantages are described below with reference to the accompanying drawings.

BRIEF DESCRIPTION OF THE DRAWINGS

FIG. 3 is a schematic diagram illustrating a method of obtaining a $T_2$-weighted magnetic resonance (MR) image using an adiabatic $T_2$ preparation sequence.

FIGS. 4A-4B illustrate amplitude and frequency components, respectively, of an adiabatic RF pulse in a representative adiabatic $T_2$ preparation sequence.

FIGS. 5A-5C are simulations for arterial blood, venous blood, and myocardium, respectively.

FIGS. 6A-6C are simulations for arterial blood, venous blood, and myocardium, respectively.

FIGS. 7A-7C are simulations for arterial blood, venous blood, and myocardium, respectively.

FIG. 10A illustrates an image acquired with two MLEV weighted $T_2$ Prep and a zoomed portion (inset) extracted from the unformatted imaging set. FIG. 10B illustrates an image acquired with adiabatic $T_2$ Prep and a zoomed portion (inset). The zoomed portion of FIG. 10B shows improvement in signal homogeneity on the proximal segment of the right coronary artery with respect to the zoomed portion of FIG. 10A.

DETAILED DESCRIPTION

As used in this application and in the claims, the singular forms "a," "an," and "the" include the plural forms unless the context clearly dictates otherwise. Additionally, the term "includes" means "comprises." Disclosed below are representative embodiments of magnetic resonance apparatus that can be configured to produce representative pulse sequences associated with adiabatic $T_2$ preparation. While particular examples and applications for the disclosed embodiments are also disclosed, the described systems, methods, and apparatus should not be construed as limiting in any way. Instead, the present disclosure is directed toward all novel and nonobvious features, aspects, and equivalents of the various disclosed embodiments, alone and in various combinations and subcombinations with one another. The disclosed systems, methods, and apparatus are not limited to any specific aspect, feature, or combination thereof, nor do the disclosed systems, methods, and apparatus require that any one or more specific advantages be present or problems be solved. In addition, the attached figures may not show the various ways in which the disclosed systems, methods, and apparatus can be used in conjunction with other systems, methods, and apparatus, and components that are well known in the art are not described in detail.

Examples of the disclosed technology include magnetic resonance (MR) methods, systems, and apparatus configured to apply adiabatic pulses to a specimen. As used herein, an adiabatic pulse is a pulse that includes an amplitude modulation and a frequency (or phase) modulation configured to produce a common nutation of substantially all water proton spins in a specimen (or spins of some other species). Such pulses can be described as electrical pulses such as radiofrequency (RF) pulses configured to produce an associated RF magnetic field that is applied to the specimen. The common nutation produced with such pulses can be achieved throughout a specimen volume even in the presence of non-uniformities in a longitudinal magnetic field $B_0$. For example, the common nutation can be obtained with magnetic field variations of up to 10%, 20%, 50%, or more. Adiabatic pulses can be associated with common nutations of about 90°, about 180°, or other angles. Adiabatic pulses associated with rotations of about 180° and 90° are referred to as adiabatic full passage (AFP) and adiabatic half passage (AHP) pulses, respectively. While typical adiabatic pulses include amplitude and frequency modulations that produce the common nutation for substantially all spins of a selected species, in some examples the modulations are selected to produce the common nutation only for spins within a selected spin bandwidth, such as, for example, 20%, 50%, 80%, or 90% of the total spin bandwidth. Pulses having such a limited bandwidth can also be referred to as pseudo-adiabatic or partially adiabatic.

Figure 2:
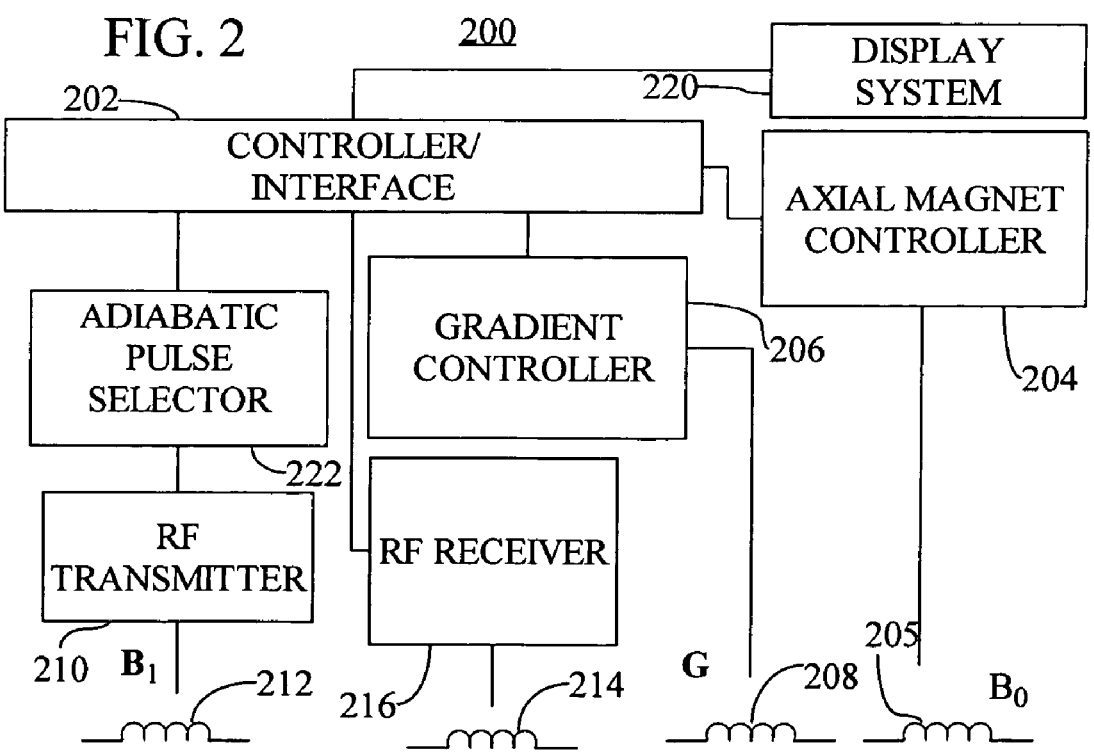
FIG. 2 is a schematic diagram of a magnetic resonance imaging system configured to select and apply adiabatic pulses in adiabatic $T_2$ preparation sequences.

A representative magnetic resonance imaging (MRI) apparatus 200 is illustrated in FIG. 2. The MRI system 200 includes a controller 202 that is typically programmed by a clinician with a series of commands corresponding to a particular imaging sequence. The command sequences can be entered with a keyboard, or a pointing device such as a mouse, or other input device. Command sequences can be stored by the controller 202 for retrieval from a hard disk, floppy disk, or other computer readable media, and can be selected from a menu, so that a clinician can easily select among an imaging protocol from various command sequences. Alternatively, command sequences or other operational information can be remotely stored and retrieved via a network connection from remote storage from, for example, a remote server.

The MRI apparatus 200 includes an axial magnet controller 204 that controls the spatial homogeneity of an axial magnetic field $B_0$ with an axial field coil 205. As used herein, the axial magnetic field $B_0$ is directed along a +z-axis in a xyz coordinate system. A plane parallel to an xy-plane (perpendicular to the z-axis) is referred to as a transverse plane. A gradient controller 206 activates a gradient coil 208 to produce a magnetic field gradient G that is typically applied as a pulse. The gradient coil 208 can consist of one or more coils or subcoils that are configured to apply particular components (such as x, y, or z-components) of the gradient field G.

A radio-frequency (RF) transmitter 210 is configured to generate RF pulses that are applied to a transmitter coil 212 to produce the RF magnetic field $B_1$. A receiver coil 214 detects changes in magnetization in the specimen and communicates the detected magnetization changes to an RF receiver 216. The RF receiver 216 processes the detected magnetization changes and provides corresponding electrical signals or image data to the controller 202 based on these changes. The particular arrangement of FIG. 2 is selected for convenience, and components of such an MRI apparatus can be arranged in other ways.

A specimen to be imaged is exposed to the axial magnetic field $B_0$, one or more field gradients G, and one or more radiofrequency fields $B_1$ that are selected by the controller 202. Changes in specimen magnetization are detected by the receiver coil 214 and processed by the RF receiver 216. The RF pulse is typically represented as product of a pulse envelope $B_1$ and a complex exponential $\exp(i\omega_{RF}t)$, wherein t is time, i is the square root of −1, and $\omega_{RF}$ is an excitation carrier frequency. The excitation frequency $\omega_{RF}$ is generally selected to be approximately equal to a resonance frequency of one or more constituents of the specimen. The resonance frequency $\omega_0$ is proportional to a product of a gyromagnetic ratio γ (a material constant) and a magnitude of the axial field $B_0$. Adiabatic RF pulses generally provide both amplitude and frequency modulation, so that the pulse envelope $B_1$ and the excitation carrier frequency $\omega_{RF}$ are time varying. For convenient implementation in some MRI systems, a pulse frequency modulation can be defined based on an associated phase modulation.

The field gradient G exposes the specimen to a non-uniform magnetic field, so that slices of the specimen can be selected for imaging. Within a selected slice, the resonance frequency $\omega_{RF}$ is sufficiently constant so that the RF receiver 216 can reject magnetization changes in non-selected slices by rejecting frequency components corresponding to the non-selected slices. Detecting changes in magnetization slice by slice permits image formation.

With only the axial magnetic field $B_0$ applied, some magnetic dipoles of sample constituents align with the axial magnetic field $B_0$ to produce an equilibrium magnetization $M_0$ that generally has only a +z-directed component. The specimen includes individual magnetic dipoles of dipole moment µ that precess about the direction of $B_0$ (the z-axis) at the frequency $\omega_0 = \gamma B_0$ that is also referred to as the Larmor frequency, wherein $B_0$ is the magnitude of the field $B_0$. Changes in magnetization are generally described with reference to an xyz coordinate system that rotates about the axial direction at the Larmor frequency. The z-axis of such a rotating coordinate system is the same as the z-axis of a stationary coordinate system while the x-axis and y-axis of the rotating coordinate system rotate in a transverse plane.

Application of a selected RF pulse can rotate a magnetization or one or more components thereof. An RF pulse of duration and magnitude at spin resonance frequency having a magnitude and duration sufficient to produce a 180 degree rotation is referred to as a 180° pulse and an RF pulse sufficient to produce a 90 degree rotation is referred to as a 90° pulse. The axis of rotation of such pulses can be selected based on the direction in which the corresponding pulse magnetic field is applied. Such RF pulses are generally referred to as "hard" pulses. Adiabatic pulses can also be applied, and are described below.

An adiabatic pulse selector 222 is configured to select adiabatic RF pulses for application with the RF transmitter 210 and the RF coil 212 as directed by the controller 202. The adiabatic pulse selector 222 is shown in FIG. 2 as a separate component, but can be included as part of the controller 202, the RF transmitter 210, or provided as a combination of these or other portions of the MRI apparatus. The adiabatic pulse selector 222 generally defines so-called "adiabatic" RF pulses in which both RF pulse amplitude and frequency (or phase) are time varying. Such pulses are configured to exhibit reduce sensitivity to inhomogeneities in $B_0$ and $B_1$. Adiabatic pulses can be selected so that magnetization vector components parallel and anti-parallel to an effective RF magnetic field $B_{eff}$ field remain substantially parallel and anti-parallel, respectively, while magnetization vector components perpendicular to the effective RF magnetic field $B_{eff}$ precess and remain substantially perpendicular to the effective RF magnetic field $B_{eff}$. Adiabatic pulses produce effective RF magnetic fields whose orientation changes more slowly than a rotation of sample magnetization about the effective RF magnetic field. Generally, the effective radiofrequency magnetic field $B_{eff}$ can be represented as a sum of the applied RF magnetic field ($B_1$) and $\Delta\omega/\gamma\check{z}$, wherein $\Delta\omega=\omega-\omega_0$, ω is an angular frequency of the applied RF magnetic field $B_1$, $\omega_0$ is a spin resonance (Larmor) frequency, γ is a gyromagnetic ratio, and ž is a unit vector parallel to the longitudinal axis. In conventional "hard" RF pulses, $\Delta\omega=0$, and the effective RF magnetic field is the same as the applied RF magnetic field $B_1$. Examples of such adiabatic pulses include so-called adiabatic fast passage (AFP) and adiabatic half-passage (AHP) RF pulses. Using adiabatic refocusing pulses a transverse magnetization can be refocused in the presence of substantial $B_1$ field inhomogeneities.

The adiabatic pulse selector 222 can select from among many adiabatic modulation functions in order to define adiabatic pulses. For example, some functions that can be used to define amplitude/frequency modulation portions of adiabatic pulses include sin/cos, tan/sec, tanh/sech, as well as numerically defined modulations such as numerically optimized modulations (NOMs). One representative AFP pulse can be defined based on a hyperbolic secant and hyperbolic tangent function pair, wherein $$B_1(t) = B_{1\,max}\,\mathrm{sech}(\beta(2t/T-1))$$

$$\Delta\omega(t) = \Delta\omega_{max}\,\tanh(\beta(1-2t/T)),$$

wherein β is a dimensionless truncation factor, typically assigned a value of about $\mathrm{sech}^{-1}(0.01)$, t is time, T is a total pulse duration, and $B_{1\,max}$ and $\Delta\omega_{max}$ are a maximum amplitude and frequency modulation, respectively. Pulse parameters such as $B_{1\,max}$ and $\Delta\omega_{max}$ can be selected based on pulse width, bandwidth, SAR deposition, RF amplifier constraints, and adiabaticity conditions. The adiabatic pulse selector 222 can include a library of adiabatic pulse definitions and/or include a processor configured to specify adiabatic pulse properties based on stored parameters, or on computed parameters.

Various adiabatic pulses can be used instead of the hyperbolic secant pulse described above. Selection of a particular pulse can be made based on application requirements. In contrast to conventional "hard" RF pulses lacking substantial frequency or phase modulation, adiabatic pulses are generally configured so that a magnetization follows the applied time-varying adiabatic RF magnetic field direction. Adiabatic pulses can refocus transverse magnetization in the presence of non-uniform $B_0$ and $B_1$. So-called $B_1$ insensitive rotation (BIR) pulses can be used that are composites of two or more pulses. For example, a BIR-3 pulse includes a first pulse segment that produces an adiabatic inversion, and a second pulse segment that compensates phase dispersion produced by the first pulse segment. This pulse produces dephasing due to off-resonance excitation, and is not generally suitable for slice selection. Other BIR pulses can have similar disadvantages. A lower power adiabatic refocusing method is based on applying substantially similar (or identical) adiabatic fast passage pulses in which a second adiabatic fast passage pulse substantially compensates phase variations generated by a first adiabatic fast passage pulse. Some functions that can be used to define adiabatic pulses include a Lorenz function, a Gaussian function, or a Hanning function.

A representative pulse sequence for coronary magnetic resonance angiography is shown in FIG. 3 and FIGS. 4A-4B. With reference to FIG. 3, a trigger pulse 302 is obtained based on, for example, an electrocardiogram (ECG). A delay period ("trigger delay) elapses prior to image or data acquisition sequences 304. A navigator beam 306, an adiabatic $T_2$ prep sequence 308, and a spectrally selective fat saturation pulse or pulse sequence 310 are applied prior to the image acquisition sequences 304. Spoiling gradients, and pulses and pulse sequences for slice selection are not shown.

The adiabatic $T_2$ prep sequence 308 is illustrated in FIGS. 4A-4B. FIG. 4A and FIG. 4B depict frequency modulation and amplitude modulation, respectively, associated with pulses in this sequence. A +90° hard RF pulse 402 rotates the z-directed magnetization into a transverse plane. The rotated magnetization is allowed to relax via both $T_1$ and $T_2$ decay during an interval TE/4, and an adiabatic pulse RF pulse 404 having an amplitude portion $404_{AM}$ and a frequency portion $404_{FM}$ is applied. The adiabatic RF pulse 404 is applied so as to establish an effective RF magnetic field $B_1$ along an effective RF B-field axis. Spins parallel or anti-parallel to the effective RF B-field axis are inverted, while spins perpendicular to the effective RF B-field axis precess and substantially remain in a plane perpendicular to the effective RF magnetic field $B_1$. The transverse magnetization dephases during the adiabatic RF pulse 404, and after an interval TE/2 the magnetization is refocused with an adiabatic pulse 406 having an amplitude portion $406_{AM}$ and a frequency portion $406_{FM}$. An accumulated phase ϕ produced by the pulse 404 can be determined as $$\phi = \int_0^T \gamma |B_{eff}(t)| dt,$$

wherein $B_{eff}(t)$ is the magnitude of the effective RF magnetic field $B_{eff}$, and γ is a gyromagnetic ratio. This phase distortion is associated with signal loss if the magnetization is returned to the longitudinal axis. As shown in FIG. 4, the adiabatic pulse 406 produces a plane rotation and compensates or partially compensates the accumulated phase shift. After another TE/4 interval, a −90° hard RF pulse 408 is applied to return isochromats to the longitudinal axis.

Simulations

Figure 1B:
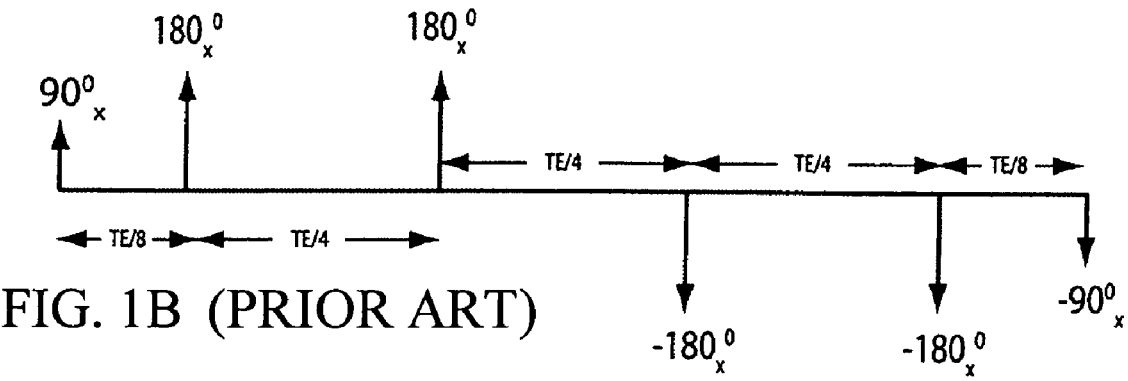
FIGS. 1A-1B illustrate standard Malcom-Levitt (MLEV) weighted $T_2$ preparation sequences.
Figure 1A:
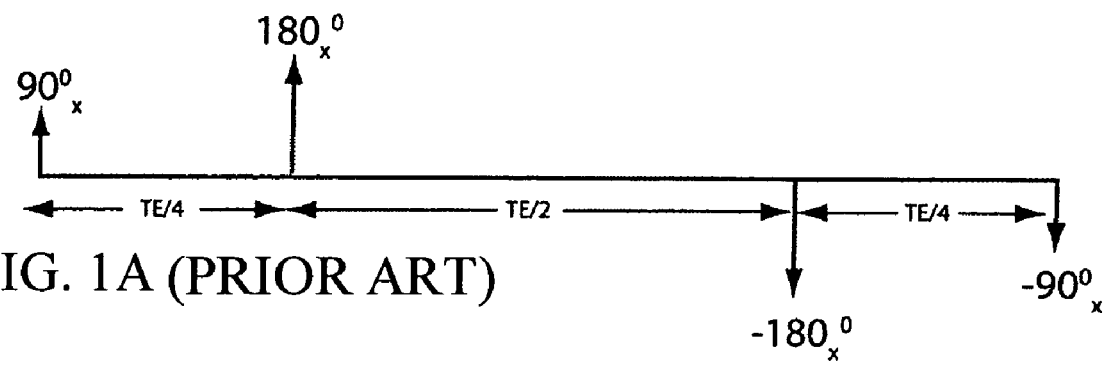

Numerical simulations were performed to obtain a normalized longitudinal magnetization $M_z/M_{eq}$ as a function of resonance offset and $B_1$ variations for the MLEV sequences of FIGS. 1A-1B and adiabatic sech/tanh pulses. The duration TE was TE=50 ms. $T_1$, $T_2$ were assumed to be 1650 ms, 100 ms (arterial blood), 1575 ms, 20 ms (venous blood), and 1114 ms, 55 ms (myocardium), respectively. The hard RF pulse was a rectangular pulse with a 0.43 ms duration. Magnetization was calculated by numerical solution of the Bloch equation. Adiabatic $T_2$ prep was based on an adiabatic sech/tanh pulse with a bandwidth of 1 kHz and a typical duration of 11 ms. The adiabatic pulses were applied to produce RF magnetizations so that one component of transverse magnetization was inverted.

Figure 5:
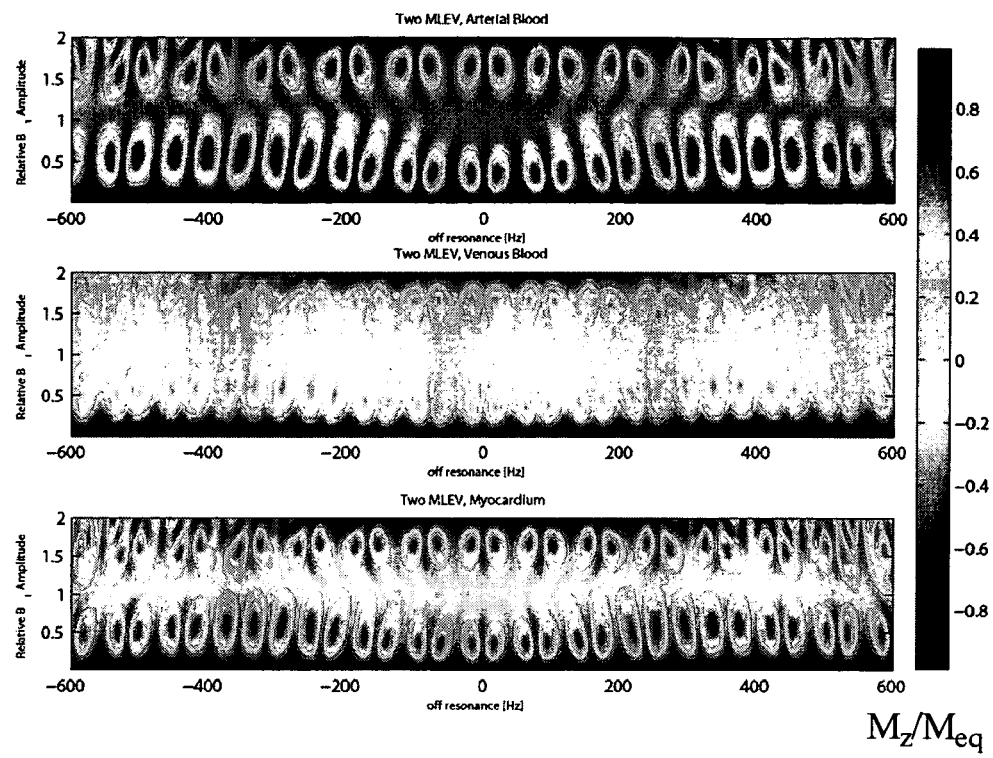
FIGS. 5A-5C show ratios of a longitudinal magnetization magnitude $M_z$ to an equilibrium magnetization magnitude $M_{eq}$ as functions of frequency offset and magnitude of an applied RF magnetic field $B_1$ obtained using numerical simulations using MLEV-based $T_2$ prep with two composite MLEV pulses. The magnitude of $B_1$ is relative to a $B_1$ magnitude required for a 90° hard pulse of duration of 0.43 ms.
Figure 6:
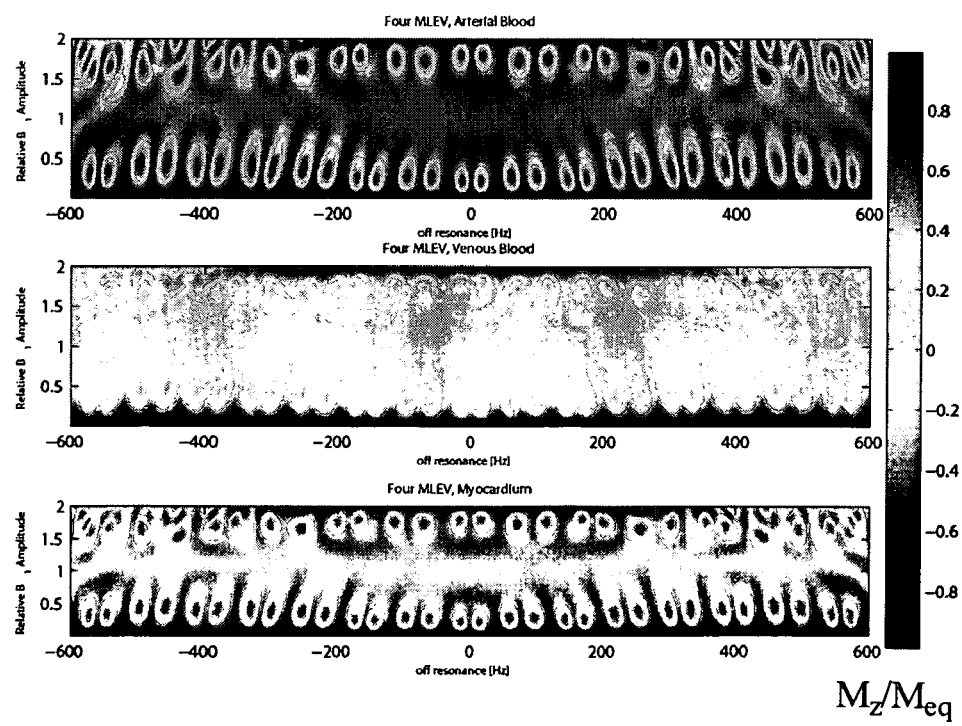
FIGS. 6A-6C show ratios of a longitudinal magnetization magnitude $M_z$ to an equilibrium magnetization magnitude $M_{eq}$ as functions of frequency offset and magnitude of an applied RF magnetic field $B_1$ obtained using numerical simulations using MLEV-based $T_2$ prep with four composite MLEV pulses. The magnitude of $B_1$ is relative to a $B_1$ magnitude required for a 90° hard pulse of duration of 0.43 ms.
Figure 7:
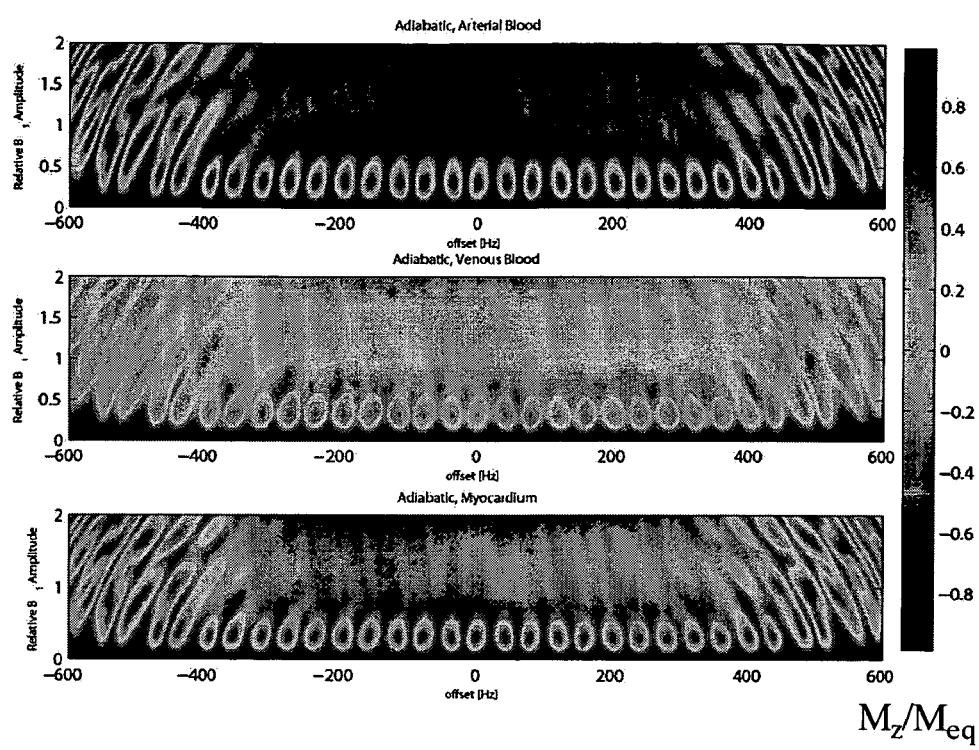
FIGS. 7A-7C show ratios of a longitudinal magnetization magnitude $M_z$ to an equilibrium magnetization magnitude $M_{eq}$ as functions of frequency offset and magnitude of an applied RF magnetic field $B_1$ obtained using numerical simulations using adiabatic $T_2$ prep. The magnitude of $B_1$ is relative to a $B_1$ magnitude required for a 90° hard pulse of duration of 0.43 ms.

Simulation results for arterial blood, venous blood, and myocardium are shown in FIGS. 5A-7A, FIGS. 5B-7B, and FIGS. 5C-7C, respectively. While the four MLEV sequence used in FIGS. 6A-6C provides superior results to that of the two MLEV sequence as shown in FIGS. 5A-5C, neither sequence is wholly satisfactory. In contrast, the adiabatic $T_2$ prep sequence used in FIGS. 7A-7C provides satisfactory normalized longitudinal magnetization for a range of frequency offsets and RF magnetic field variations. Although a sech/tanh adiabatic pulse was used to obtain these simulation results, other adiabatic pulses can be used.

Example Images

Coronary MR angiography was performed on normal volunteers with no known coronary disease. Images were obtained with a PHILLIPS 3.0 T INTERA MRI system equipped with QUASAR DUAL gradients (maximum amplitude of 80 mT/m and maximum slew rate of 200 mT/m/ms) using a 6-element cardiac phase-array receiver coil. A vector electrocardiogram was used for R-wave detection and gating. A scout scan was acquired for coronary artery localization and navigator positioning using a gradient echo imaging sequence. An ECG triggered, segmented steady-state free precession (SSFP) cine images (TR=3.8 ms, TE=1.8 ms, α=45° and temporal resolution of 39.6 ms) at the level of the proximal-to-mid right coronary artery (RCA) for visual determination of the most quiescent period was then performed. Consequently, a 3D low resolution, navigator gated scan for localization of the coronaries was acquired. A 2D-selective RF pulse with 12 revolutions in k-space and a beam radius of 15 mm was used for gating and tracking of respiratory motion. The navigator beam was positioned at the dome of the right hemidiaphragm with an acceptance window of 5 mm, and RF excitation angle of 30. Images were obtained from each volunteer using adiabatic $T_2$ prep, MLEV $T_2$ prep, and without $T_2$ prep.

Image analysis was performed on a stand alone personal computer, and images were reconstructed using a research software application SOAPBUBBLE described in A. Etienne et al., "'Soap-Bubble' Visualization and Quantitative Analysis of 3d Coronary Magnetic Resonance Angiograms," Magn. Res. Med. 48:658-666 (2002). Contrast-to-noise ratio (CNR) and signal-to-noise ratio (SNR) were calculated using individual slices from 3D data sets. Regions of interest (ROI) were selected in the ostium of a right coronary artery for measuring a mean ($S_{blood}$) and a standard deviation ($N_{blood}$) of the blood signal. A mean $S_{muscle}$ and a standard deviation $N_{muscle}$ within the ROI in the septum were used to calculate the CNR of blood muscle. CNR and SNR were calculated as follows:

$$SNR = \frac{S_{blood}}{N_{blood}}$$

$$CNR = \frac{S_{blood} - S_{muscle}}{0.5(N_{blood} + N_{muscle})}.$$

Figures 8A, 8B, 8C:
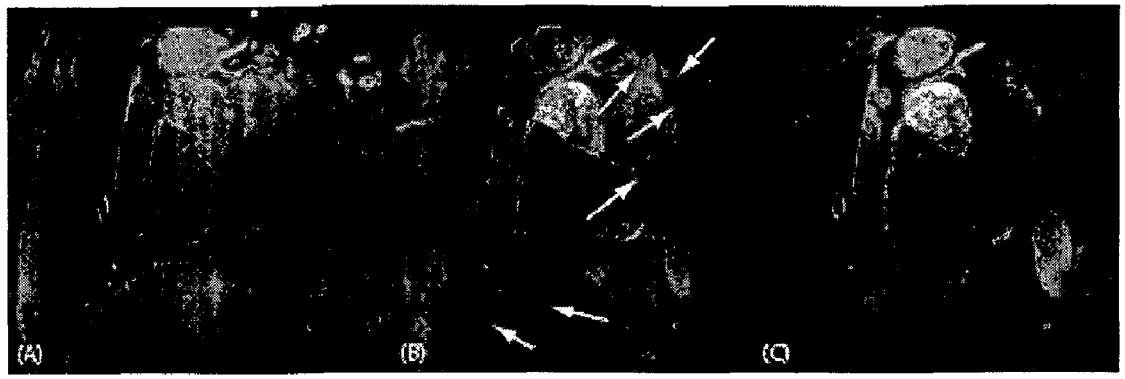
FIGS. 8A-8C are illustrative right coronary magnetic resonance angiograms (MRAs) obtained without $T_2$ prep, with conventional MLEV weighted composite $T_2$ prep (two pulses), and with adiabatic $T_2$ prep, respectively.

Sample images of a right coronary artery of a normal volunteer obtained without $T_2$ prep, with standard MLEV $T_2$ prep, and adiabatic $T_2$ prep as described above, respectively, are shown in FIGS. 8A-8C. The sample magnetic resonance angiogram (MRA) of FIG. 8A exhibits no $B_1$ inhomogeneity artifacts, but lacks contrast between coronary arteries and surrounding tissues. FIG. 8B shows enhanced contrast, but has significant artifacts in the liver, myocardium, and coronary tree. These artifacts (some of which are noted with arrows in FIG. 8B) are associated with field inhomogeneity. FIG. 8C shows excellent contrast without the artifacts of FIG. 8B.

Figures 9A, 9B, 9C:
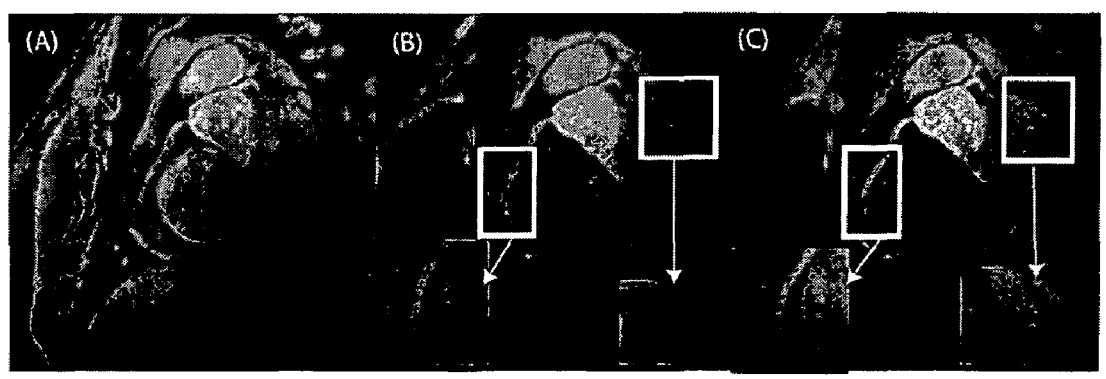
FIGS. 9A-9C are additional illustrative right coronary magnetic resonance angiograms (MRAs) obtained without $T_2$ prep, with conventional MLEV weighted composite $T_2$ prep (two pulses), and with adiabatic $T_2$ prep, respectively.
Figures 10A, 10B:
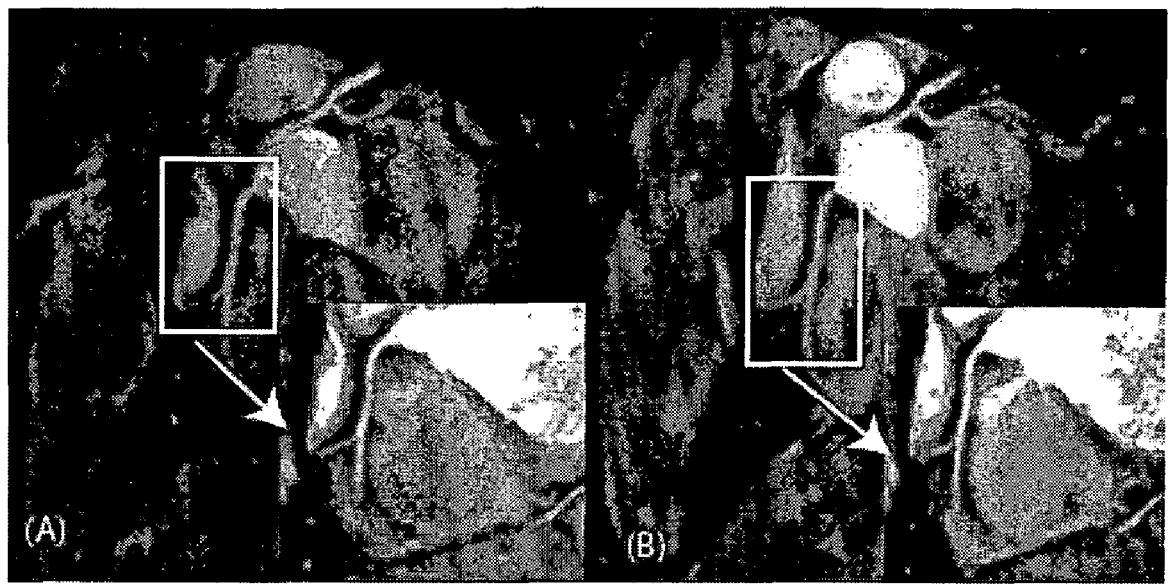
FIGS. 10A-10B are example right coronary MRAs.

FIGS. 9A-9C are additional coronary angiography images acquired from a normal volunteer without $T_2$ prep, with standard MLEV T$_2$ prep, and adiabatic T$_2$ prep, respectively. Superior visualization of distal branches in both the right and left coronary artery systems is apparent in the image obtained with adiabatic T$_2$ prep.

Representative methods and apparatus based on adiabatic T$_2$ prep are described above. These methods and apparatus are illustrative, and are not to be taken as limiting. For example, in other embodiments, hard 90° pulses and hard 180° pulses can be replaced with adiabatic half passage pulses and adiabatic full passage pulses, respectively. In additional embodiments, composite pulses can also be used instead of hard pulses. Some principles of the disclosed technology are described with reference to particular adiabatic pulse waveforms, but other adiabatic, quasi-adiabatic, partially adiabatic and/or pseudo-adiabatic pulses can be used. Typically, adiabatic pulses such as adiabatic full passage pulses and adiabatic half passage pulses produce magnetization rotations of about 180° and 90°, respectively, for a range of B$_1$ field strengths, and thus produce rotations that are substantially independent of B$_1$ field strength. Such adiabatic pulses have sufficient bandwidth to refocus substantially all spins in a sample. Other pulses and pulse sequences such as partially adiabatic pulses as described in, for example, JMR 156:26 or pseudo-adiabatic pulses as described in, for example, Beaudoin and Côté, "The pseudo-adiabatic RF pulse: a fast adiabatic quality RF pulse with low SAR," Proc. Intl. Soc. Mag. Reson. Med. 10 (2002) and Barker et al., "Broadband Proton Decoupling for In Vivo Brain Spectroscopy in Humans," Mag. Reson. Med. 45:226-232 (2001). Pseudo-adiabatic pulses are generally based on a sequence of RF pulses applied along a respective series of axes. For example, a series of 1, . . . , Np pulses applied in a yz plane at angles of 90/(Np+1), . . . , 90Np/(Np+1) with respect to the z-axis can effectively rotate a longitudinal magnetization (a z-directed magnetization) into the transverse plane. A set of such sequentialized RF pulses can be referred to generally as a pseudo-adiabatic pulse or pseudo-adiabatic pulse sequence.

In view of these variations, it will be apparent that the disclosed embodiments can be modified in arrangement and detail without departing from the scope of the disclosure, and we claim all that is encompassed by the appended claims.

We claim:

1. A magnetic resonance imaging method, comprising:
    with a radio-frequency (RF) coil, applying a magnetic field so as to rotate at least a portion of a longitudinal magnetization of a specimen into a transverse plane throughout a specimen volume to establish a transverse magnetization;
    allowing the transverse magnetization to evolve for a time period of about T$_E$/4;
    selecting a first adiabatic radio-frequency (RF) pulse having an amplitude modulation and a frequency modulation;
    applying an RF magnetic field based on the first adiabatic RF pulse so as to substantially invert a component of the transverse magnetization;
    allowing the inverted transverse magnetization to evolve for a time period of about T$_E$/2;
    selecting a second adiabatic radio-frequency (RF) pulse having an amplitude modulation and a frequency modulation;
    applying an RF magnetic field based on the second adiabatic RF pulse so as to substantially invert a component of the transverse magnetization;
    allowing the inverted transverse magnetization to evolve for a time period of about T$_E$/4;
    rotating at least a portion of the transverse magnetization so as to produce a stored T$_2$-weighted longitudinal magnetization; and
    obtaining a specimen image associated with the specimen volume based on the stored T$_2$-weighted longitudinal magnetization.

2. The method of claim 1, wherein the first and second adiabatic RF pulses have a common amplitude modulation and a common frequency modulation.

3. The method of claim 2, wherein the rotation of the longitudinal magnetization into the transverse plane is accomplished with a composite 90° pulse.

4. The method of claim 1, wherein the rotation of the longitudinal magnetization into the transverse plane is accomplished with an adiabatic half passage pulse.

5. The method of claim 1, wherein the rotation of the longitudinal magnetization into the transverse plane is accomplished with a pseudo-adiabatic half passage pulse.

6. The method of claim 1, wherein at least one of the amplitude modulation and the frequency modulation is based on a numerically defined adiabatic waveform.

7. The method of claim 1, wherein the amplitude modulation is based on a hyperbolic secant function, and the frequency modulation is based on a hyperbolic tangent function.

8. The method of claim 1, wherein the specimen includes at least a portion of a heart.

9. The method of claim 1, wherein the specimen image is a portion of a cardiac system and the specimen image is based on the stored magnetization produced in a single cardiac cycle.

10. The method of claim 9, further comprising applying the pulses in response to an electrocardiogram signal.

11. The method of claim 1, further comprising displaying an image based on the image signal.

12. A non-transitory computer readable storage medium containing computer executable instructions for a method comprising:
    rotating at least a portion of a longitudinal magnetization of a specimen into a transverse plane with a composite 90° pulse to establish a transverse magnetization throughout a specimen volume;
    selecting a first adiabatic radio-frequency (RF) pulse having an amplitude modulation and a frequency modulation;
    applying an RF magnetic field based on the first adiabatic RF pulse so as to substantially invert a component of the transverse magnetization;
    allowing the inverted transverse magnetization to evolve;
    selecting a second adiabatic radio-frequency (RF) pulse having an amplitude modulation and a frequency modulation;
    applying an RF magnetic field based on the second adiabatic RF pulse so as to substantially invert a component of the transverse magnetization;
    allowing the inverted transverse magnetization to evolve for a time period of about T$_E$/4;
    rotating at least a portion of the transverse magnetization so as to produce a stored T$_2$-weighted longitudinal magnetization; and
    obtaining a specimen image based on the stored T$_2$-weighted longitudinal magnetization.

13. A magnetic resonance system, comprising:
    a system controller configured to define an adiabatic pulse configured to invert a component of a transverse sample magnetization and a pulse sequence that includes a first 90° pulse, a first instance of the adiabatic pulse, a second instance of the adiabatic pulse, and a second 90° pulse with temporal separations of TE/4, TE/2, and TE/4, wherein TE is an echo time;

a radio-frequency (RF) coil configured to produce an RF magnetic field pulse sequence based on the pulse sequence defined by the system controller so as to produce a $T_2$-weighted longitudinal specimen magnetization throughout a specimen volume;

a receiver coil configured to produce a detected signal based on the $T_2$-weighted longitudinal specimen magnetization produced in response to the pulse sequence; and an image processor configured to produce a $T_2$-weighted specimen image based on the detected signal.

14. The magnetic resonance system of claim 13, wherein the system controller is configured to define at least one of the first 90° pulse or the second 90° pulse as a composite pulse.

15. The magnetic resonance system of claim 13, wherein the system controller includes a user interface configured to receive user input associated with selection of the adiabatic pulse.

16. The magnetic resonance system of claim 13, wherein the system controller includes a computer readable medium having stored thereon a plurality of adiabatic pulse definitions, and the system controller is configured to define the adiabatic pulse by selecting from among the plurality of adiabatic pulse definitions.

17. The magnetic resonance system of claim 13, wherein the system controller is configured to select an echo time that is associated with a $T_2$-weighted image signal.

18. The magnetic resonance imaging system of claim 13, wherein the adiabatic pulse is defined based on a first function and a second function that define an amplitude modulation portion and a frequency modulation portion, respectively, of the adiabatic pulse definition.

19. The magnetic resonance imaging system of claim 13, further comprising a trigger input configured to receive a trigger signal associated with an electrocardiogram.

20. The magnetic resonance system of claim 13, wherein the controller is configured to produce an image of a sample that includes at least a portion of a cardiac system based on the detected signal associated with the $T_2$-weighted specimen magnetization in a single cardiac cycle.

21. The magnetic resonance system of claim 20, further comprising a display configured to display an image based on the image signal.

22. A method of reducing magnetic resonance image sensitivity in a $T_2$-weighted image to variations in an applied magnetic field, comprising:

applying a first 90° pulse with a radio-frequency (RF) coil;

applying a first adiabatic pulse after an interval of about TE/4, wherein TE is an echo time;

applying a second adiabatic pulse after an interval of about TE/2;

applying a second 90° pulse after an interval of about TE/4 to produce a stored $T_2$-weighted longitudinal magnetization; and obtaining a $T_2$-weighted image signal based on the stored $T_2$-weighted longitudinal magnetization.

23. The method of claim 22, wherein the first and second 90° pulses are adiabatic half passage pulses.

24. The method of claim 22, wherein the first and second 90° pulses are pseudo-adiabatic half passage pulses.

25. The method of claim 22, wherein the first and second 90° pulses are composite 90° pulses.

26. The method of claim 22, wherein the first adiabatic pulse and the second adiabatic pulses have a common waveform.

27. The method of claim 26, wherein the common waveform is defined by a pair of functions that define an amplitude portion and a frequency portion.

28. The method of claim 26, wherein the common waveform is defined by a numerically defined amplitude modulation and a numerically defined frequency modulation.

29. The method of claim 22, further comprising processing the image signal to produce a coronary magnetic resonance angiogram.

30. The method of claim 22, wherein the series of pulses is applied to-at least a portion of a cardiac system to produce the stored longitudinal magnetization and the image signal is obtained during a single cardiac cycle.

* * * * *